(12) United States Patent
Forsbring (10) Patent No.: US 7,882,797 B2
(45) Date of Patent: Feb. 8, 2011

(54) METHOD AND DEVICE FOR APPLICATION OF PARTICLES IN AN ABSORBENT STRUCTURE

(75) Inventor: Göran Forsbring, Kungsbacka (SE)

(73) Assignee: SCA Hygiene Products AB, Gothenburg (SE)

( * ) Notice: Subject to any disclaimer, the term of this patent is extended or adjusted under 35 U.S.C. 154(b) by 268 days.

(21) Appl. No.: 12/085,956

(22) PCT Filed: Dec. 15, 2005

(86) PCT No.: PCT/SE2005/001946

§ 371 (c)(1),
(2), (4) Date: Jun. 3, 2008

(87) PCT Pub. No.: WO2007/069956

PCT Pub. Date: Jun. 21, 2007

(65) Prior Publication Data

US 2009/0074960 A1    Mar. 19, 2009

(51) Int. Cl.
*B05B 7/00* (2006.01)
(52) U.S. Cl. .................. 118/308; 118/300; 251/283; 427/203
(58) Field of Classification Search ................. 427/197; 118/300, 308; 251/283
See application file for complete search history.

(56) References Cited

U.S. PATENT DOCUMENTS

| | | | |
|---|---|---|---|
| 2,056,266 A * | 10/1936 | Goodell | 423/204 |
| 4,138,161 A * | 2/1979 | Payne | 406/155 |
| 5,102,585 A | 4/1992 | Pieper et al. | |
| 5,248,524 A | 9/1993 | Soderlund | |
| 5,279,854 A * | 1/1994 | Kendall et al. | 427/197 |
| 5,567,472 A | 10/1996 | Siegfried et al. | |

FOREIGN PATENT DOCUMENTS

EP    1 053 729 A1    11/2000

OTHER PUBLICATIONS

PCT/ISA/210.
PCT/ISA/237.
PCT/IPEA/409.

* cited by examiner

*Primary Examiner*—Parviz Hassanzadeh
*Assistant Examiner*—Albert Hilton
(74) *Attorney, Agent, or Firm*—Buchanan Ingersoll & Rooney PC (57) ABSTRACT

An apparatus and a method for applying particles within a pre-determined limited area of an absorbent structure. The apparatus has: a nozzle arranged to dispense the particles on the pre-determined limited area of the absorbent structure; conduit for supplying particles by a gas flow from a particle container to the nozzle; a valve arranged between the nozzle and the particle container; and, a valve vane arranged to direct the gas flow having particles through the valve from a particle inlet to an application outlet when the valve is in a first position and to direct the gas flow having particles through the valve from the particle inlet to a residue outlet when the valve is in a second position. The apparatus also has a device for maintaining a gas flow in the application outlet when the valve is in the second position.

19 Claims, 6 Drawing Sheets

Fig. 1
PRIOR ART

PRIOR ART

METHOD AND DEVICE FOR APPLICATION OF PARTICLES IN AN ABSORBENT STRUCTURE

TECHNICAL FIELD

The present disclosure relates to an apparatus and a method for applying particles in an absorbent structure and relates, specifically, to an apparatus allowing for applying particles within a pre-determined limited area of an absorbent structure as well as a method for such application.

BACKGROUND

There is today a variety of absorbent articles, such as sanitary napkins, panty liners, diapers, bed protections and incontinence guards, having different shapes and dimensions on the market. Such an absorbent article usually comprises an absorbent structure formed to absorb body fluids under a short period of time and to distribute and store body fluids. This means that the absorbent structure usually comprises several different layers having different characteristics in relation to each other. The absorbent structure often comprises at least a liquid acquisition layer, a liquid storage layer and a liquid distribution layer.

As a liquid acquisition layer is usually used a porous material having a high momentaneous liquid receiving capacity. Examples of such materials are cellulosic fluff pulp of thermomechanic or chemothermomechanic (CTMP) type, chemically stiffened cellulosic fibres, synthetic fiber structures of different types and porous foam materials etc.

As a storage layer is usually cellulosic fluff pulp mixed with so called superabsorbents used, or superabsorbent polymer particles (SAP), i.e. crosslinked polymers having the ability to absorb several times their own weight (10 times or more).

As distribution layer may cellulosic fluff pulp, tissue layer, foam, synthetic fibers and the like having high liquid distribution capacity be used. It is also possible to combine two or more of the functions acquisition, storage and distribution in one and the same layer.

Since superabsorbent particles are more expensive than natural or synthetic fibermaterials, it is advantageous to reduce the amount of superabsorbent particles in the absorbent structure. Rather than reduce the amount of such particles throughout the entire structure, it is desirable to distribute the particles in the structure in a pre-determined manner such that the particles are where it is most efficient to receive and store body fluids.

Figure 1:
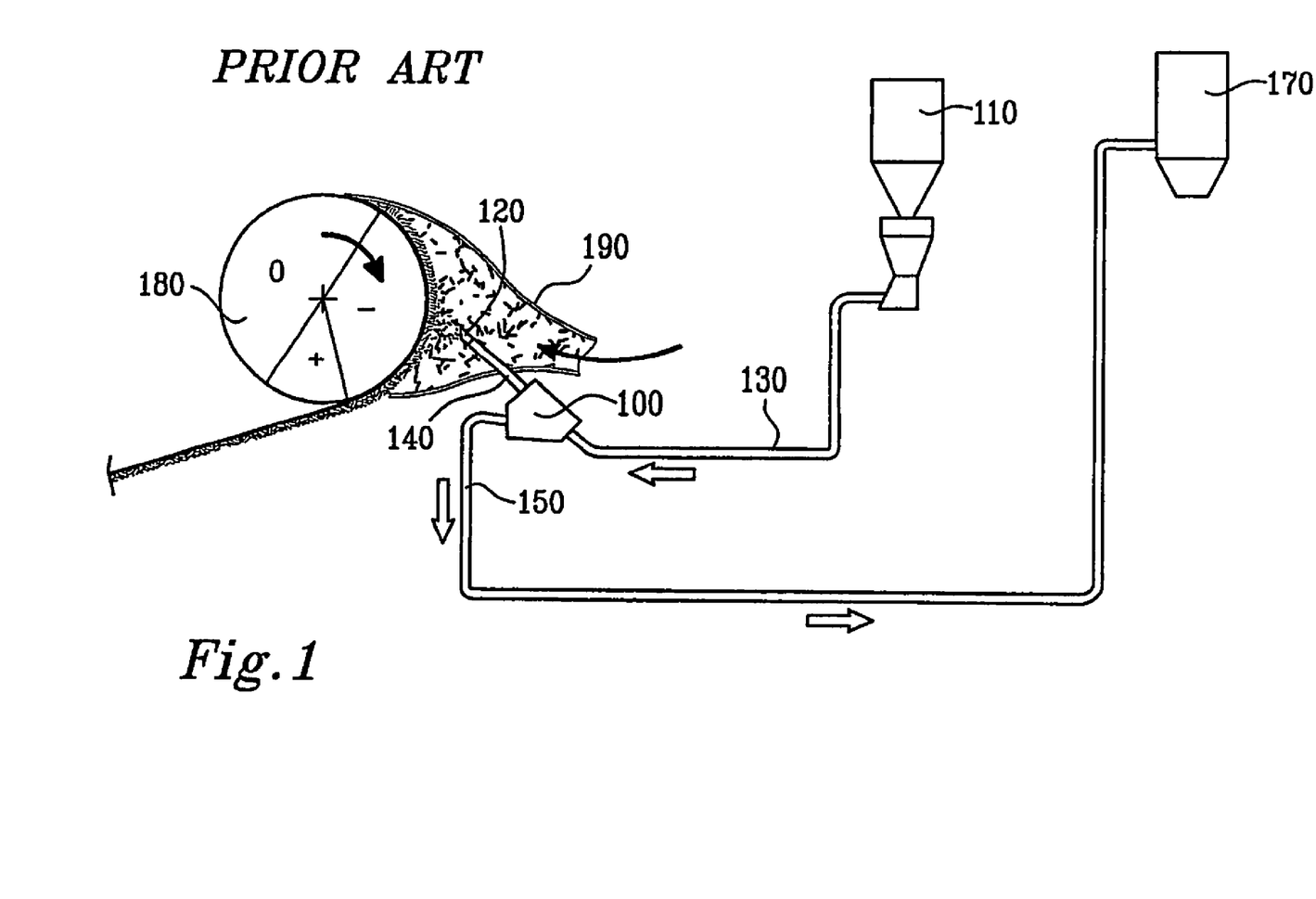
FIG. 1 shows a system comprising a prior art valve for applying particles on a fibrous material.

In order to be able to apply the superabsorbent particles on pre-determined areas of the absorbent structure, commonly airborne superabsorbent particles are directed through a valve, where the supplying of particles to the absorbent structure is controlled by means of a valve vane. Such an apparatus for applying particles on an absorbent structure is shown in FIG. 1. When a valve vane arranged in the valve is in a first position, the airborne particles are directed through the valve to a nozzle supplying the particles to the absorbent structure. When the valve vane is in a second position, the airborne particles are directed through the valve to a collecting container for recycling of the particles. This kind of valve is shown in more detail with the valve vane in the first position in FIG. 2a and in the second position in FIG. 2b.

Such a valve is previously known through U.S. Pat. No. 5,279,854, which displays an apparatus for applying superabsorbent particles on pre-determined areas of a fibrous material. Air-entrained absorbent particles are directed through a valve which alternately is directing the particles to a first and a second nozzle supplying the particles to the absorbent structure, which allows the particles to de deposited on the absorbent structure on pre-determined areas.

However, it has turned out that when a valve of the kind described above is in its second position, the particles that are in the outlet conduit when the valve is switched to the second position will be dispensed on the fibrous material forming a "tail" to the pre-determined area, a so called tailing effect. It is desirable to get rid of this "tail" and obtain a distinct ending of the particle provided areas of the absorbent structure, in order to reduce the consumption of particles and at the same time make an aesthetically attractive effect. Further, particles in the "tail" may even end up outside the absorbent structure, e.g. directly between a surface material and a back layer. Since superabsorbent particles often form sharp granules, it may in this case cause discomfort at use of the article, which is yet another reason for desiring to avoid the forming of a tail of particles.

OBJECTS AND SUMMARY

An object of the present disclosure is to provide an improved apparatus for giving a particle flow a distinct trailing edge, which particle flow comprises particles for application within a pre-determined limited area of an absorbent structure.

This object has been achieved through an apparatus according to embodiments of the present disclosure.

A further object of the present disclosure is to provide an improved method for giving a particle flow a distinct trailing edge, which particle flow comprises particles for application within a pre-determined limited area of an absorbent structure.

This further object has been achieved through a method according to embodiments of the present disclosure.

According to the disclosure a gas flow may be maintained in the outlet conduit when the valve is in its second, i.e. its closed position. This leads to the particles in the outlet conduit when the valve switches to the second position getting the same outlet speed as the other particles had. In this manner the problem of the "tailing effect" described above in connection with previously known valves is avoided, where not only the particle flow in the outlet conduit but also the airflow transporting the particles is throttled when the valve is in its second position. In the prior art valves, the last particles will be deposited with a lower outlet speed than the particles where the air pressure is kept on a maximum, leading to a "tail" formed by the last particles.

According to the disclosure a "tailing effect" may be avoided and the application of particles may, thus, be controlled in a more pre-determined manner.

Still other objects and features of the present disclosure will become apparent from the following detailed description considered in conjunction with the accompanying drawings. It is to be understood, however, that the drawings are designed solely for purposes of illustration and not as a definition of the limits of the disclosure. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings like reference characters denote similar elements throughout the several views and.

DETAILED DESCRIPTION OF PREFERRED EMBODIMENTS

A prior art system for applying particles to an absorbent structure is shown in FIG. 1, where a rotating mat-forming wheel 180 is used to form fibrous material into an absorbent structure for use in an absorbent article, such as sanitary napkins, panty liners, diapers, bed protections and incontinence guards. A hood 190 is arranged above the mat-forming wheel 180 to which fibrous material for the forming of the actual absorbent structure is carried. The mat-forming wheel comprises in a conventional manner moulds into which fibrous material is sucked by means of an under pressure for the forming of discrete absorption bodies. In the hood 190 is further a nozzle 120 arranged, which dispenses superabsorbent polymer particles within a pre-determined area during forming of the absorbent body. The nozzle 120 is further connected to an outlet conduit 140 wherein airborne particles are transported.

The actual apparatus for supplying the particles comprises a particle container (not shown) from which particles are transferred to a feeder 110, e.g. by means of a vacuum pump (not shown). The feeder 110 may, for example, be of a vibrator feeder or screw feeder type. The feeder 110 is arranged to feed an even pre-determined amount of particles per unit of time. From the feeder the particles are transported by means of gas, preferably air, through a pipe system to the nozzle 120. The transporting gas flow (airflow) is created, e.g. by means of pneumatically driven ejectors, pumps including ejectors or by using a fan (not shown in FIG. 1). Between the feeder 110 and the nozzle 120 a diverting valve 100 is arranged. The diverting valve 100 is in a first position directing airborne particles from the feeder 110 to the nozzle 120, and in a second position the diverting valve is directing the airborne particles from the feeder 110 to a collecting container 170. The particles returning to the collecting container 170 are then recycled. The pipe system comprises a particle transport conduit 130 connected to the feeder 110 and the valve 100, an outlet conduit 140 arranged between the valve 100 and the nozzle 120 and, a return conduit 150 arranged between the valve 100 and the collecting container 170.

Figure 2A:
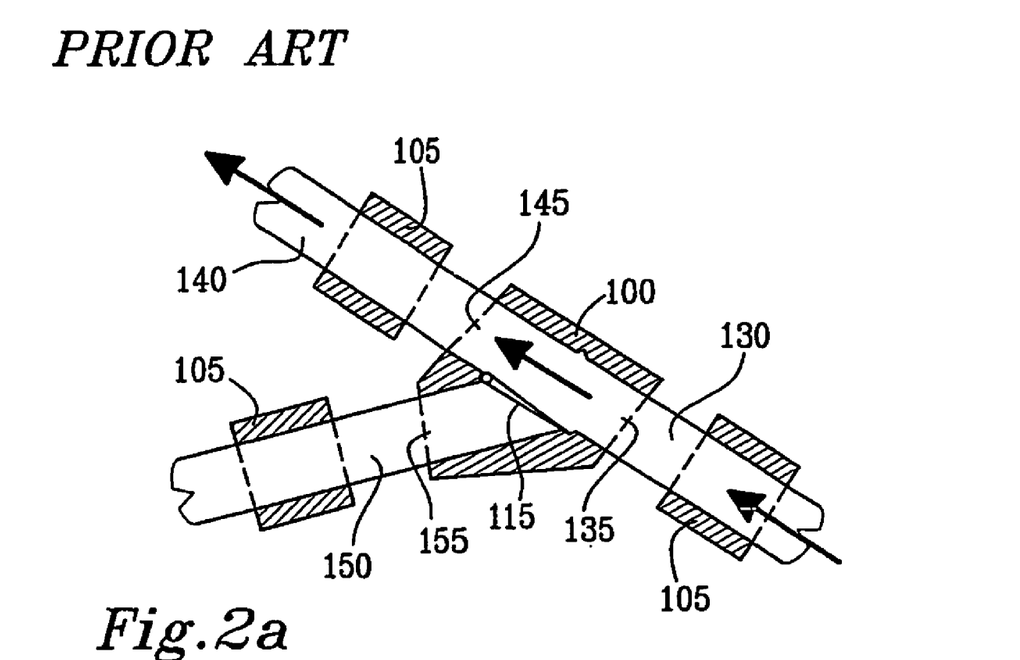
FIGS. 2a and 2b are a cross-sectional view of a prior art valve in a first and a second position respectively.
Figure 2B:
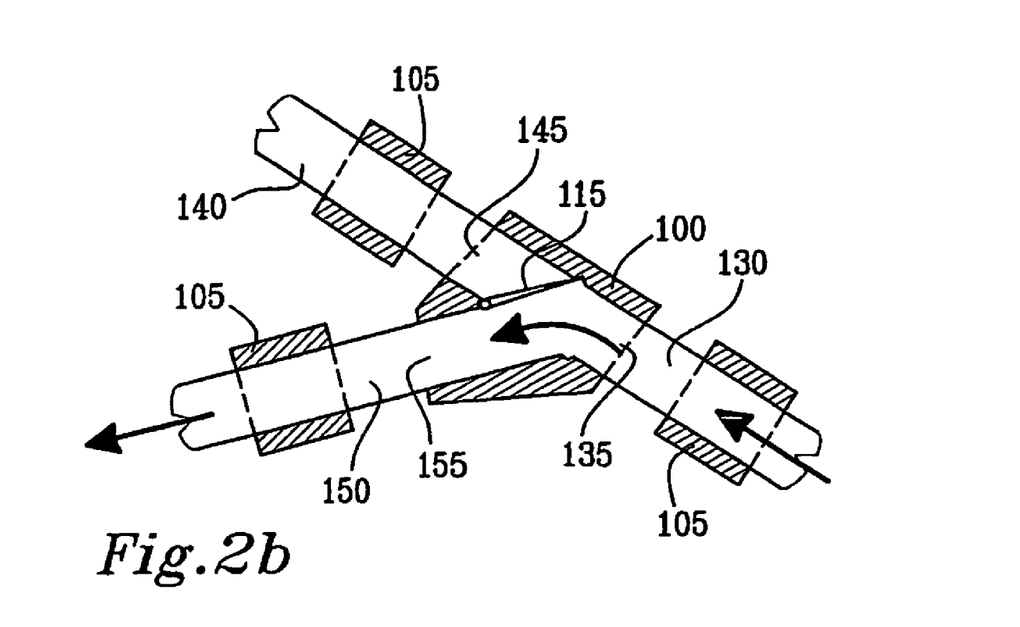

FIGS. 2a and 2b show in cross-section the prior art valve 100 in a first and a second position respectively. The valve 100 comprises a particle inlet 135 connected to the particle transport conduit 130, an application outlet 145 connected to the outlet conduit 140 and, a residue outlet 155 connected to the return conduit 150. Arranged in the valve 100 is a valve vane 115 which is arranged to alternately direct the airborne particle flow to the application outlet 145 and the residue outlet 155. The valve vane is e.g. controlled by means of a pneumatic cylinder or a servo-motor. In FIGS. 2a and 2b are also shown three ejectors 105 arranged at the inlet 135 and at the outlets 145 and 155 respectively.

In order to apply the particles on a pre-determined position of the fibrous material, i.e applying an intermittent SAP layer on an absorbent structure, so called zoning, the airborne particle flow is controlled by alternately setting the valve in a first and a second position. However, it has turned out that the SAP layer gets a badly defined trailing edge having a long drawn-out tail when such a valve is used. The inventors of the present disclosure have realized that the reason for this is that when the valve is set in its second position not only the particle flow in the outlet conduit is throttled but also the airflow transporting the particles. This leads to the particles which are in the outlet conduit when the valve is set in the second position getting a lower speed than the other particles where the air pressure is on a maximum. The effect of a throttled airflow is that the last particles supplied to the absorbent structure are forming a tail, a so called "tailing effect".

Figure 3:
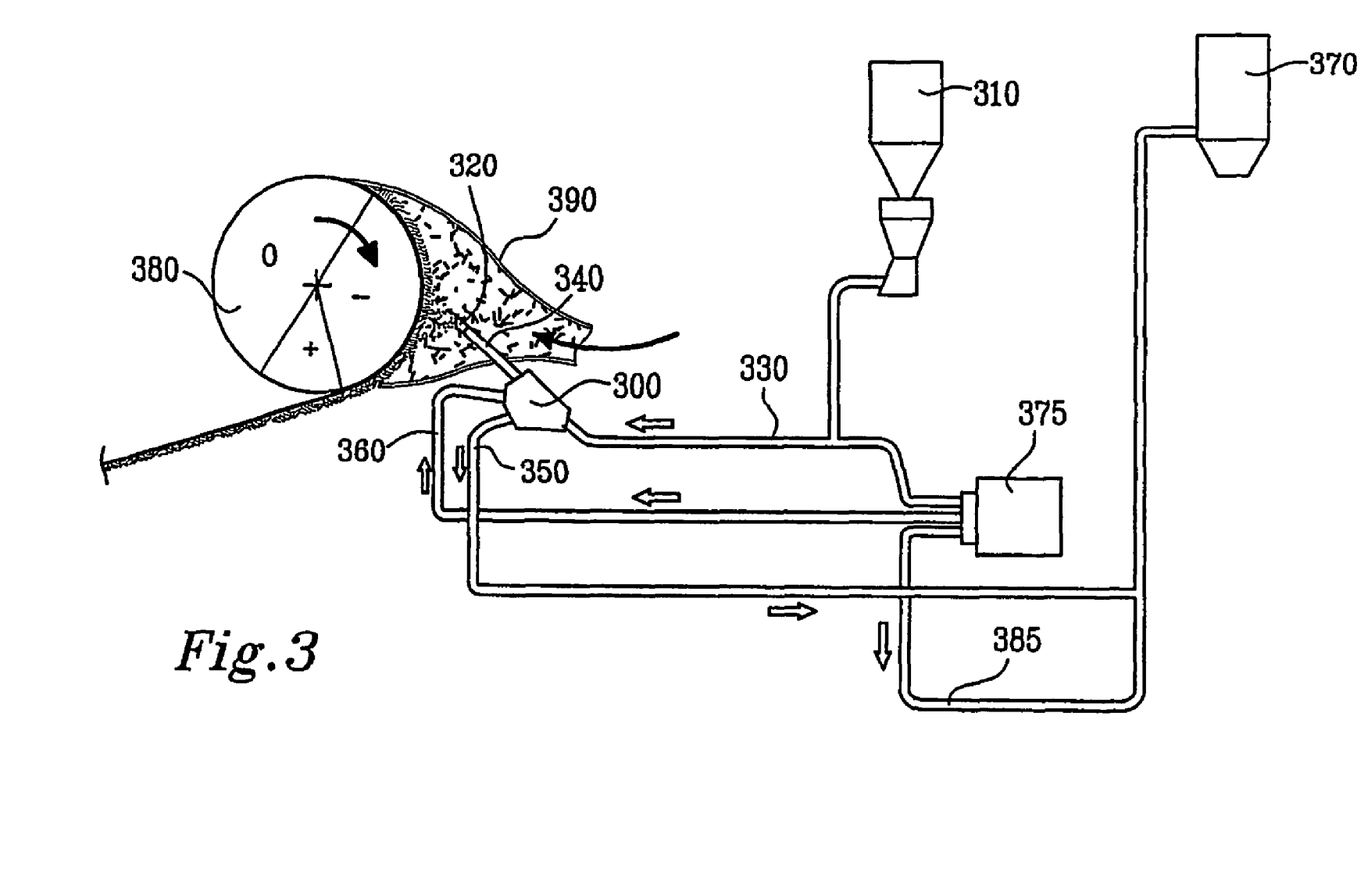
FIG. 3 shows a system comprising an inventive apparatus for applying particles on a fibrous material.

One example of an inventive apparatus for applying particles, especially SAP particles, on a fibrous material is shown in FIG. 3, where a rotating mat-forming wheel 380 is used to form fibrous material into an absorbent structure for use in an absorbent article, such as sanitary napkins, panty liners, incontinence guards, diapers and bed protections. A hood 390 is arranged above the mat-forming wheel 380 to which fibrous material for the forming of the actual absorbent structure is carried. The mat-forming wheel comprises in a conventional manner moulds into which fibrous material is sucked by means of an under pressure for the forming of discrete absorption bodies. In the hood 390 is further a nozzle 320 arranged, which dispenses superabsorbent polymer particles within a pre-determined area during forming of the absorption body. The nozzle 320 is further connected to an outlet conduit 340, also called particle application conduit, wherein airborne particles are transported. The nozzle 320 may be placed on different locations in the hood 390, depending on the desired location of the pre-determined area for the particles.

The actual apparatus for supplying the particles comprises a particle container (not shown) from which particles are transferred to a feeder 310, e.g. by means of a vacuum pump (not shown). The feeder 310 may, for example, be of a vibrator feeder or screw feeder type. The feeder 310 is arranged to feed an even pre-determined amount of particles per unit of time. From the feeder the particles are transported by means of gas, preferably air, through a pipe system to the nozzle 320. The transporting gas flow (airflow) is created, e.g. by means of pneumatically driven ejectors, pumps including ejectors or by using a fan. In the example shown in FIG. 3, a fan 375 is used for creating the airflow. Between the feeder 310 and the nozzle 320 a diverting valve 300 is arranged, which in this exemplifying figure correspond to the valve shown in FIGS. 5a and 5b. The diverting valve 300 is in a first position directing airborne particles from the feeder 310 to the nozzle 320, and in a second position the diverting valve 300 is directing the airborne particles from the feeder 310 to a collecting container 370. The particles returning to the collecting container 370 are then recycled.

The pipe system comprises a particle inlet conduit 330 connected to the feeder 310 and the valve 300, an application outlet conduit 340 arranged between the valve 300 and the nozzle 320 and, a residue outlet conduit 350, herein a return conduit, arranged between the valve 300 and the collecting container 370. The pipe system further comprises a particle-free inlet conduit 360 connected to the valve 300, which transports clean carrier gas without particles and which is arranged between the valve 300 and the fan 375. In the figure is also shown a second gas conduit 385 arranged at the fan 375 and connected to the residue outlet conduit 350 in order to assist the returning particle flow to the collecting container 370. The carrier gas may suitably be air.

Figure 4A:
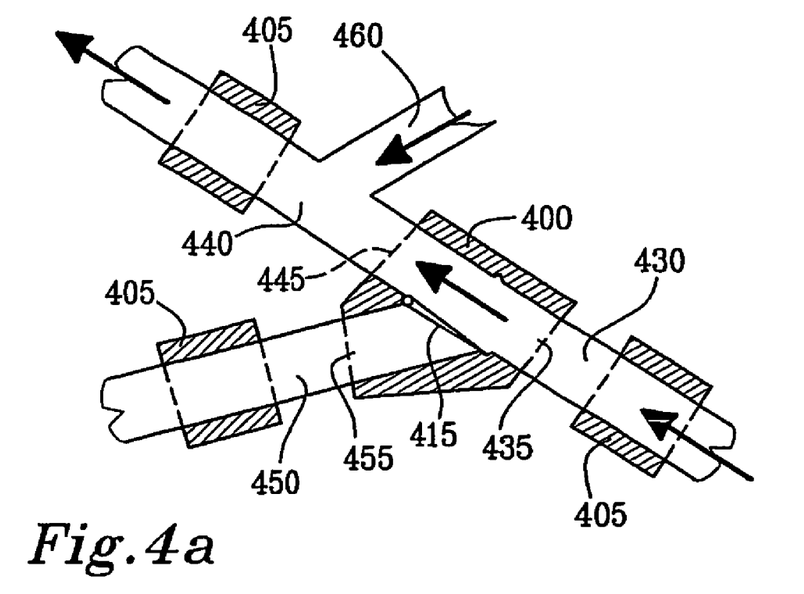
FIGS. 4a and 4b are a cross-sectional view of a first embodiment of an inventive valve in a first and a second position respectively.
Figure 4B:
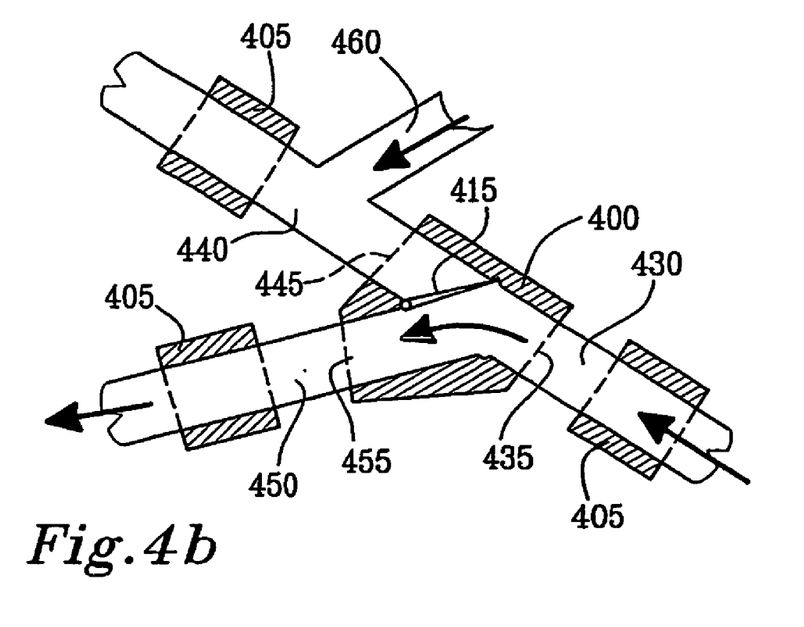

A first preferred embodiment of the present disclosure is shown in the FIGS. 4*a* and 4*b*, wherein a valve 400 comprises a valve vane 415, a particle inlet 435, an application outlet 445 and a residue outlet 455. The valve vane is pivotally arranged between the application outlet 445 and the residue outlet 455 and is e.g. controlled by means of a pneumatic cylinder or a servo-motor (not shown in the figures). The particle inlet 435 is communicating with the feeder (shown in FIG. 3) via the particle inlet conduit 430 in which the airborne particles are transported from the feeder. The application outlet 445 is communicating with the nozzle (shown in FIG. 3) via the connected particle application conduit 440. The residue outlet 455 is communicating with the particle collector (shown in FIG. 3) via the residue outlet conduit 450, which herein is a return conduit in which airborne particles are returned. The particle-free inlet conduit 460 is in the first preferred embodiment connected to the particle application conduit 440 to which it leads. In the particle-free inlet conduit 460 clean air is transported, i.e. without particles, and thereby is guaranteed that the airflow in the particle application conduit 440 not is throttled but is maintained when the valve vane switches position. In the embodiment shown in FIG. 4*a* and 4*b* the airflow is created by means of three pneumatically driven ejectors 405 arranged at the particle inlet 435 and at outlets 445 and 455 respectively.

FIG. 4*a* shows the valve 400 in its first position when the valve vane 415 is closing the residue outlet 455. When the valve 400 is in its first position, the airborne particles are, thus, directed from the particle inlet 435 through the valve to the application outlet 445 and thereafter through the particle application conduit 440 where they are mixed with the extra supplied air from the particle-free inlet conduit 460 and further to the nozzle for dispensing on the fibrous material.

FIG. 4*b* shows the valve 400 in its second position when the valve vane 415 is closing the application outlet 445. When the valve 400 is in the second position the airborne particles are directed from the particle inlet 435 through the valve 400 to the residue outlet 455 and thereafter to the return conduit 450 for further transport to the collecting container. At the same time, clean carrier gas is guided from the particle-free inlet conduit 460 through the particle application conduit 440 making sure that possibly left particles are dispensed in an even pace.

Figure 5A:
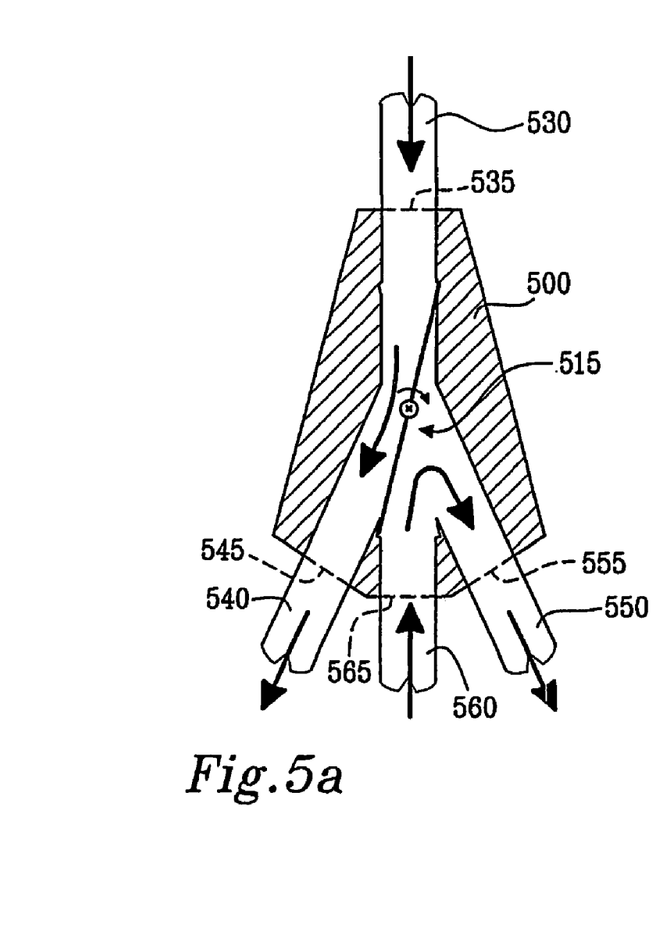
FIGS. 5a and 5b are a cross-sectional view of a second embodiment of an inventive valve in a first and a second position respectively.
Figure 5B:
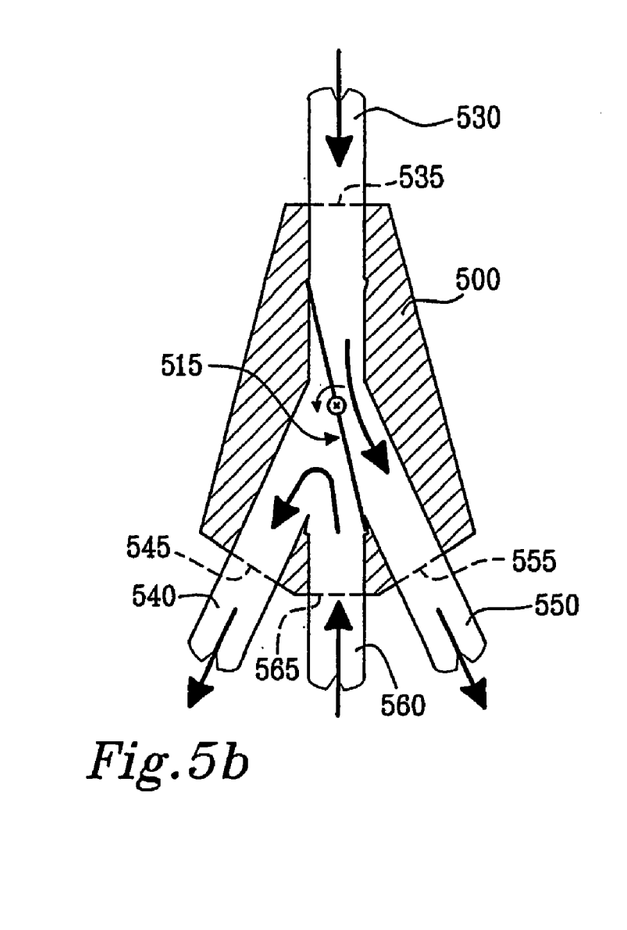

A second preferred embodiment of the present disclosure is shown in FIGS. 5*a* and 5*b*, wherein a valve 500 comprises a valve vane 515, a particle inlet 535, an application outlet 545 and a residue outlet 555. The valve vane is pivotally arranged on a shaft and is e.g. controlled by means of a pneumatic cylinder or a servo-motor (not shown in the figures). The particle inlet 535 is communicating with the feeder (shown in FIG. 3) via the particle inlet conduit 530 in which the airborne particles are transported from the feeder. The application outlet 545 is communicating with the nozzle (shown in FIG. 3) via the connected particle application conduit 540. The residue inlet 555 is communicating with the particle collector (shown in FIG. 3) via the residue outlet conduit 550, in which airborne particles are returned. The valve 500 further comprises a particle-free inlet 565 connected to a particle-free inlet conduit 560 in which clean air, i.e. without particles, is transported. The particle-free inlet 565 is herein arranged between the application outlet 545 and the residue outlet 555 downstream the valve vane 515.

FIG. 5*a* shows the valve 500 in its first position when the valve vane 515 is set such, that the airborne particles are directed through the valve 500 from the particle inlet 535 to the application outlet 545 and further on to the nozzle (not shown in FIG. 5*a*) to be mixed with the fibrous material in the absorption body. Particle-free air is at the same time directed through the valve from the particle-free inlet 565 to the residue outlet 555 and further on to the residue outlet conduit 550.

FIG. 5*b* shows the valve 500 in its second position when the valve vane is set such that the airborne particles are directed through the valve 500 from the particle inlet 535 to the residue outlet 555 and further on to the collecting container (not shown in FIG. 5*b*). Clean air is at the same time directed in through the valve 500 from the particle-free inlet 565 to the application outlet 545 and thus guarantees that the airflow in the application outlet conduit 540 not is throttled but is maintained when the valve is in its second position.

The valve according to the second embodiment of the disclosure gives a stable airflow towards the mat-forming wheel without pulsations irrespective of if the valve is in the first or second position.

Figure 6A:
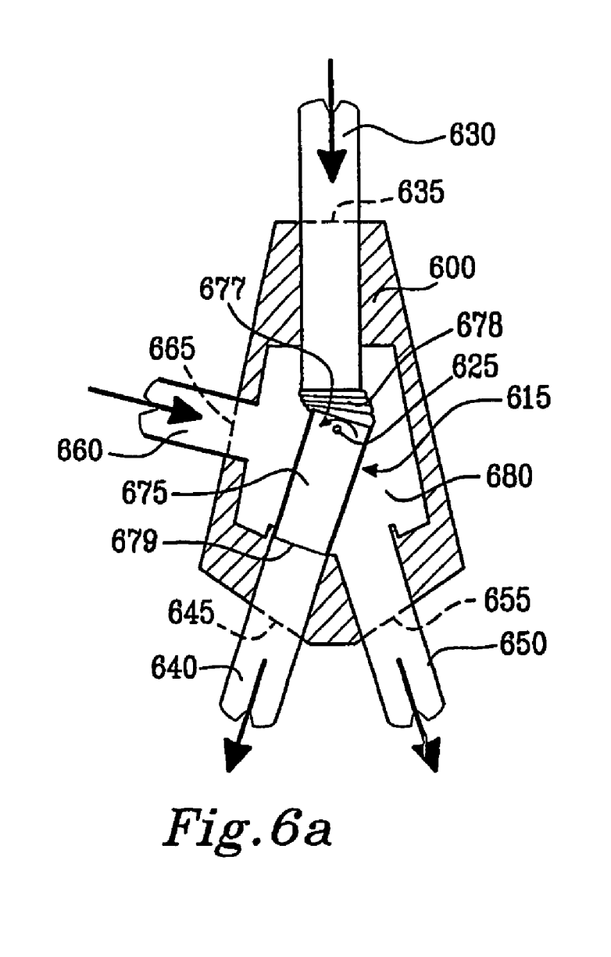
FIGS. 6a and 6b are a cross-sectional view of a third embodiment of an inventive valve in a first and a second position respectively.
Figure 6B:
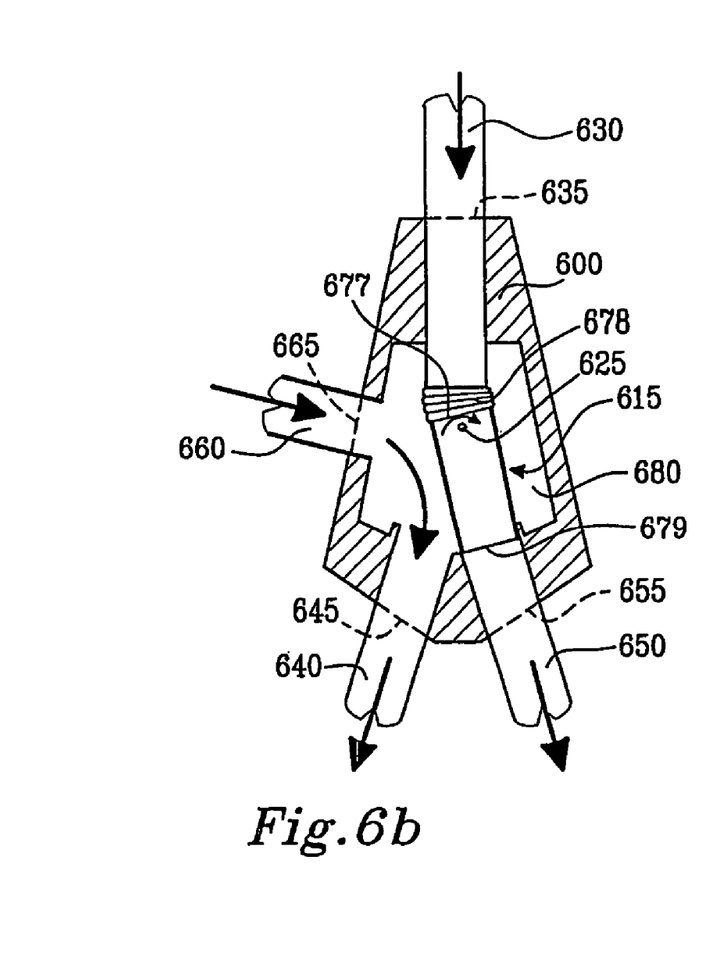

According to a third embodiment shown in FIGS. 6*a* and 6*b*, the valve 600 comprises a chamber 680, whereby the chamber 680 comprises a particle inlet 635, a particle-free inlet 665, an application outlet 645 and a residue outlet 655.

Inside the chamber 680, the particle inlet 635 is connected to a tubular member 675 via a flexible bellows 678. The tubular member 675 is in its first end 677 suspended around an axis 625, whereby the tubular member 675 is pivotal around the axis 625.

When the tubular member 675 is pivoted, the second end 679 of the tubular member 675 is moved from the application outlet 645 to the residue outlet 655 (or the other way around), whereby the tubular member 675 forms the valve vane 615. Pivoting of the tubular member 675 is e.g. controlled by means of a pneumatic cylinder or a servo-motor, or the like (not shown in the figures).

The length of the tubular member 675 is adapted such that the second end 679 of the tubular member 675 connects to the application outlet 645 when the tubular member 675 is in its first outer position (shown in FIG. 6*a*) and connects to the residue outlet 655 when the tubular member 675 is in its second outer position (shown in FIG. 6*b*).

The application outlet 645 is communicating with the nozzle (shown in FIG. 3) via the connected particle application conduit 640. The residue outlet 655 is communicating with the particle collector (shown in FIG. 3) via the residue outlet conduit 650, in which airborne particles are returned. The valve 600 further comprises a particle-free inlet 665 connected to a particle-free inlet conduit 660 in which clean air, i.e. without particles, is transported.

FIG. 6*a* shows the valve 600 in its first position when the valve vane 615 (tubular member 675) is set such, that the airborne particles are directed through the valve 600 from the particle inlet 635 to the application outlet 645 and further on to the nozzle (not shown in FIG. 6*a*). The particle-free air is at the same time directed into the valve 600 from the particle-free inlet 665 through the chamber 680 and out through the residue outlet 655.

FIG. 6*b* shows the valve 600 in its second position when the valve vane 615 (tubular member 675) is set such, that the airborne particles are directed through the valve 600 from the particle inlet 635 to the residue outlet 655 and further on to the collecting container. The particle-free air is at the same time directed in through the valve 600 from the particle-free inlet 665 through the chamber 680 to the application outlet 645 and thus guarantees that the airflow in the application outlet conduit 640 not is throttled but is maintained.

The shown embodiment in FIGS. 6a and 6b also guarantees an even airflow towards the mat-forming wheel.

An inventive method for applying particles within a pre-determined limited area of an absorbent structure comprises the steps of: supplying particles by means of a gas flow from a particle container; dispensing the particles on the pre-determined limited area of the absorbent structure by means of a nozzle; providing a valve between the nozzle and the particle container; directing the gas flow comprising particles through the valve from a particle inlet to an application outlet connected to a particle application conduit when the valve is in a first position; directing the gas flow comprising particles through the valve from the inlet to a residue outlet connected to a residue outlet conduit when the valve is in a second position; and maintaining a gas flow through the application outlet conduit when the valve is in the second position.

Variations of the method are clear from the above described embodiments of the inventive apparatus.

It is realized that several variations are possible within the scope of the disclosure. E.g. the shape of the valve vane may vary, just as the geometrical arrangement of inlet and outlet conduits. The application of particles may be done in one or several areas in or on the absorbent structure. The inventive apparatus and the method have in the shown embodiments been used with a mat-forming wheel for forming of the absorbent structure. The apparatus and method may, however, be used also with other manufacturing methods of the absorbent structure, such as application of particles on a web material, e.g. a fibrous material.

The invention claimed is:

1. An apparatus for applying particles within a pre-determined limited area of an absorbent structure, which apparatus comprises:
 a nozzle arranged to dispense the particles on the pre-determined limited area of the absorbent structure;
 conduit for supplying particles by a gas flow from a particle container to the nozzle;
 a valve arranged between the nozzle and the particle container;
 a valve vane arranged to direct the gas flow comprising particles through the valve from a particle inlet to an application outlet when the valve is in a first position and to direct the gas flow comprising particles through the valve from the particle inlet to a residue outlet when the valve is in a second position;
 wherein the apparatus further comprises a device for maintaining a gas flow in the application outlet when the valve is in the second position;
 said device for maintaining a gas flow comprises a particle-free inlet in the valve, which particle-free inlet is arranged to supply a particle-free gas flow;
 wherein the particle-free inlet is arranged between the application outlet and the residue outlet downstream of the valve vane, whereby the valve vane is arranged to change the direction of the particle-free gas flow through the valve with a change in the valve vane from the first position to the second position, to direct the particle-free gas flow through the valve from the particle-free inlet to the application outlet when the valve is in the second position and to direct the particle-free gas flow from the particle-free inlet to the residue outlet when the valve is in the first position.

2. An apparatus for applying particles within a pre-determined limited area of an absorbent structure, which apparatus comprises:
 a nozzle arranged to dispense the particles on the pre-determined limited area of the absorbent structure;
 conduit for supplying particles by a gas flow from a particle container to the nozzle;
 a valve arranged between the nozzle and the particle container;
 a valve vane arranged to direct the gas flow comprising particles through the valve from a particle inlet to an application outlet when the valve is in a first position and to direct the gas flow comprising particles through the valve from the particle inlet to a residue outlet when the valve is in a second position;
 wherein the apparatus further comprises a device for maintaining a gas flow in the application outlet when the valve is in the second position;
 said device for maintaining a gas flow comprises a particle-free inlet in the valve, which particle-free inlet is arranged to supply a particle-free gas flow;
 wherein the valve vane is formed as a tube flexibly connected to the particle inlet and arranged to direct the particle flow from the particle inlet to the application outlet when the valve is in the first position, and from the particle inlet to the residue outlet when the valve is in the second position; and
 wherein the valve vane is arranged to change the direction of the particle-free gas flow through the valve with a change in the valve vane from the first position to the second position, to direct the particle-free gas flow through the valve from the particle-free inlet to the application outlet when the valve is in the second position and to direct the particle-free gas flow from the particle-free inlet to the residue outlet when the valve is in the first position.

3. The apparatus according to claim 1, whereby the application outlet is connected to a particle application conduit and the residue outlet is connected to a residue outlet conduit, whereby the device for maintaining a gas flow in the application outlet maintains a gas flow in the application outlet conduit when the valve is in the second position.

4. The apparatus according to claim 1, whereby a particle-free inlet conduit is connected to the particle-free inlet in the valve for supplying a particle-free gas flow.

5. The apparatus according to claim 2, whereby the particle-free gas flow from the particle-free inlet is guided to the residue outlet when the valve is in the first position, and to the application outlet when the valve is in the second position.

6. The apparatus according to claim 1, whereby said residue outlet conduit is arranged to transport the gas flow comprising particles to a collecting arrangement for recycling of the particles.

7. The apparatus according to claim 1, whereby the apparatus further comprises at least one pneumatically driven ejector arranged to create said gas flow.

8. The apparatus according to claim 1, whereby the apparatus further comprises at least one fan arranged to create said gas flow.

9. The apparatus according to claim 1, whereby said gas is air.

10. The apparatus according to claim 1, whereby said particles are superabsorbent polymer particles.

11. The apparatus according to claim 2, whereby the application outlet is connected to a particle application conduit and the residue outlet is connected to a residue outlet conduit, whereby the device for maintaining a gas flow in the application outlet maintains a gas flow in the application outlet conduit when the valve is in the second position.

12. The apparatus according to claim 2, whereby a particle-free inlet conduit is connected to the particle-free inlet in the valve for supplying a particle-free gas flow.

13. The apparatus according to claim 2, whereby said residue outlet conduit is arranged to transport the gas flow comprising particles to a collecting arrangement for recycling of the particles.

14. The apparatus according to claim 2, whereby the apparatus further comprises at least one pneumatically driven ejector arranged to create said gas flow.

15. The apparatus according to claim 2, whereby the apparatus further comprises at least one fan arranged to create said gas flow.

16. The apparatus according to claim 2, whereby said gas is air.

17. The apparatus according to claim 2, whereby said particles are superabsorbent polymer particles.

18. The apparatus according to claim 1, wherein the valve vane is arranged to prevent the particle-free gas flow from entering the application outlet when the valve vane is in the first position and to prevent the particle-free gas flow from entering the residue outlet when the valve vane is in the second position.

19. The apparatus according to claim 2, wherein the valve vane is arranged to prevent the particle-free gas flow from entering the application outlet when the valve vane is in the first position and to prevent the particle-free gas flow from entering the residue outlet when the valve vane is in the second position.

* * * * *